United States Patent
Pedersen et al.

(10) Patent No.: US 8,221,324 B2
(45) Date of Patent: Jul. 17, 2012

(54) RECONFIGURABLE WIRELESS ULTRASOUND DIAGNOSTIC SYSTEM

(75) Inventors: Peder C. Pedersen, Sterling, MA (US); Philip Cordeiro, Providence, RI (US); Reginald James Duckworth, Shrewsbury, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 472 days.

(21) Appl. No.: 12/299,540

(22) PCT Filed: May 4, 2007

(86) PCT No.: PCT/US2007/068234
§ 371 (c)(1),
(2), (4) Date: Apr. 14, 2009

(87) PCT Pub. No.: WO2007/131163
PCT Pub. Date: Nov. 15, 2007

(65) Prior Publication Data
US 2010/0022882 A1    Jan. 28, 2010

Related U.S. Application Data

(60) Provisional application No. 60/798,440, filed on May 5, 2006.

(51) Int. Cl.
*A61B 8/00* (2006.01)

(52) U.S. Cl. .................. 600/459; 367/188; 361/679.02; 361/679.03

(58) Field of Classification Search .................. 600/459, 600/437, 446; 367/135, 137, 903, 910, 188; 361/679.02, 679.03; 345/7, 8; 2/94, 95, 2/102, 253
See application file for complete search history.

(56) References Cited

U.S. PATENT DOCUMENTS

| | | | |
|---|---|---|---|
| 6,196,003 B1 * | 3/2001 | Macias et al. | 62/3.7 |
| 6,532,152 B1 * | 3/2003 | White et al. | 361/692 |
| 6,540,682 B1 | 4/2003 | Leavitt et al. | |
| 6,780,154 B2 | 8/2004 | Hunt et al. | |
| 6,962,566 B2 | 11/2005 | Quistgaard et al. | |
| 6,980,419 B2 | 12/2005 | Smith et al. | |
| 7,141,020 B2 | 11/2006 | Poland et al. | |
| 2002/0014420 A1 * | 2/2002 | Schultz et al. | 206/305 |
| 2003/0139671 A1 * | 7/2003 | Walston et al. | 600/437 |
| 2005/0018540 A1 | 1/2005 | Gilbert et al. | |
| 2005/0215892 A1 | 9/2005 | Emery et al. | |
| 2005/0228281 A1 | 10/2005 | Nefos | |
| 2005/0251035 A1 | 11/2005 | Wong et al. | |
| 2006/0058652 A1 | 3/2006 | Little | |
| 2006/0115689 A1 * | 6/2006 | Lee | 429/9 |

OTHER PUBLICATIONS

Sebastian et al. Development of a field-deployable voice-activated ultrasound scanner system. Proceedings of the IEEE 30th Annual Northeast Bioengineering Conference. p. 47-48. Apr. 17, 2004.*
ISR/WO, PCT/US2007/068234, mailing date: Sep. 4, 2008, Reconfigurable Wireless Untrasound Diagnostic System, Intl. FD: May 4, 2007.
U.S. Appl. No. 60/798,440, Reconfigurable Wireless Ultrasound Diagnostic System, filed May 5, 2006.

* cited by examiner

*Primary Examiner* — Parikha Mehta
(74) *Attorney, Agent, or Firm* — Burns & Levinson LLP; Jacob N. Erlich

(57) ABSTRACT

An untethered ultrasound imaging system having selectable command control and wireless component connection and image transmission. Ultrasound data collected by the ultrasound system can be augmented with additional sensor data.

24 Claims, 13 Drawing Sheets

RECONFIGURABLE WIRELESS ULTRASOUND DIAGNOSTIC SYSTEM

CROSS REFERENCE TO RELATED APPLICATIONS

This application is a U.S.C. §371 of PCT/US2007/068234 filed May 4, 2007 and claims priority under 35 U.S.C. §119 from provisional application Ser. No. 60/798,440 entitled RECONFIGURABLE WIRELESS ULTRASOUND DIAGNOSTIC SYSTEM, filed on May 5, 2006.

STATEMENT OF GOVERNMENT INTEREST

This invention was made with United States Government support from TATRC (Telemedicine and Advanced Technology Research Center), under contract number DAMD17-03-0006. The United States Government has certain rights in the invention.

BACKGROUND OF THE INVENTION

The present invention relates to an untethered ultrasound imaging system having selectable command control, and wireless component connection and image transmission. Ultrasound data gathered by the ultrasound system can be augmented with additional sensor data.

SUMMARY OF THE INVENTION

The needs set forth above as well as further and other needs and advantages are addressed by the present invention. The solutions and advantages of the present invention are achieved by the illustrative embodiment described herein below.

For a better understanding of the present invention, together with other and further objects thereof, reference is made to the accompanying drawings and detailed description. The scope of the present invention is pointed out in the appended claims.

DETAILED DESCRIPTION OF THE PREFERRED EMBODIMENTS

The present invention is now described more fully hereinafter with reference to the accompanying drawings, in which the illustrative embodiment of the present invention is shown. The following configuration description is presented for illustrative purposes only. Any computer configuration satisfying the speed and interface requirements herein described may be suitable for implementing the system of the present invention.

Figure 1:
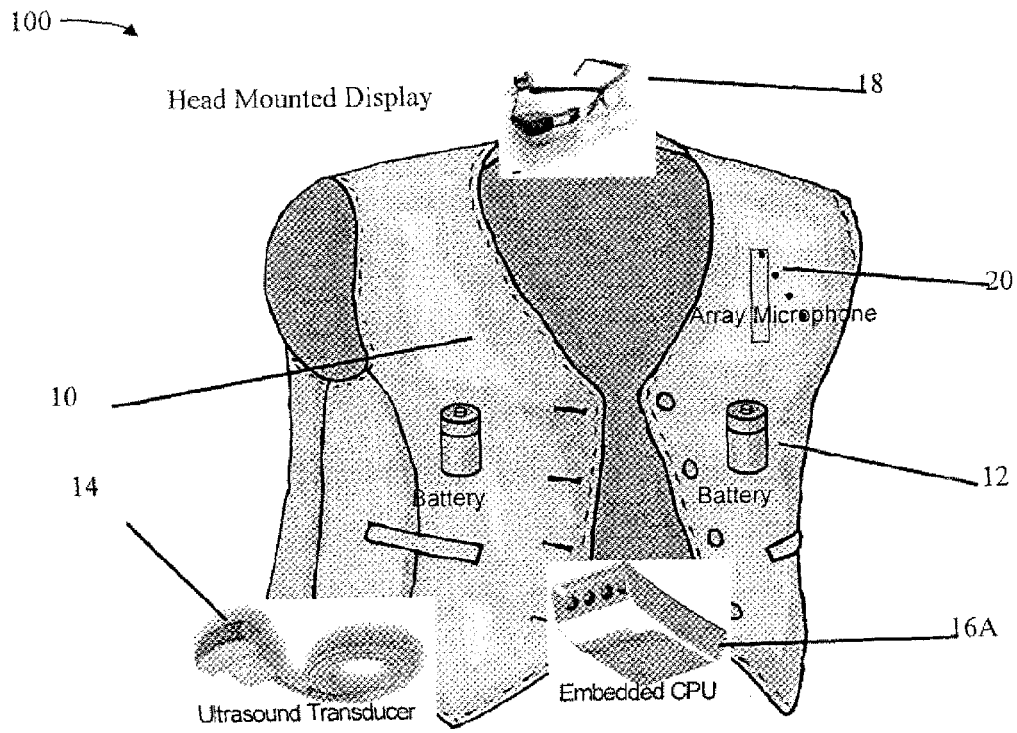
FIG. 1 is a pictorial diagram of an illustrative use-specific entity, a vest, and the positioning of illustrative components of the invention.
Figure 2:
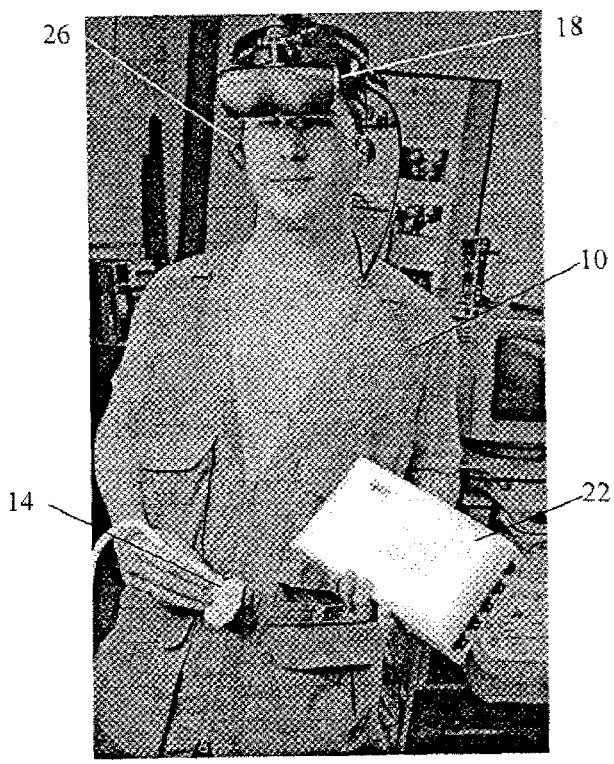
FIG. 2 is a pictorial diagram of an illustrative use-specific entity, a vest, ready for use.

Referring now to FIGS. 1 and 2, system 100 can include, but is not limited to including, an output device such as, for example, head mounted display, also referred to as headset, 18, an input device, for example, array microphone 20, a use-specific entity, for example, vest 10, a power source, for example, Li-Ion batteries 12, ultrasound transducer 14 operating with an ultrasound imaging system such as Terason 2000/3000, ultrasound front end 23 (FIG. 8), and embedded computer 16A which can be a dual core processor with a hardware accelerator. Note that this specification does not limit the invention to a single type of transducer, any type of transducer that satisfies the requirements of the invention can be used. Algorithms that take a significant amount of time to process can be implemented in a parallel fashion to take advantage of an optional dual core processor. System 100 requires no infrastructure, such as access to power, table or desk. System 100 is not limited to the use of Terason 2000/3000, rather it can encompass any ultrasound system that can be implemented in a modular fashion.

System 100 can provide an ultrasound diagnostic system having untethered imaging, command control by, for example, voice, and image management, for example, wirelessly. In FIG. 2, vest 10 is shown in use. Headset (also referred to herein as viewer) 18 is the illustrative output device for this application. Vest 10 could include embedded cabling, batteries 12 could be positioned in breast pockets, ultrasound transducer 14 and front end 23 (FIG. 8) could be positioned in lower front pockets, and embedded computer 16A could be positioned in the back of vest 10, for example, attached to a belt. In the general case, the use-specific entity can be configured to hold enclosure 22, power supply 21 (FIG. 8), input device 45 (FIG. 8), and ultrasound transducer 14 and front end 23. To accompany the use-specific device, headset 18 can be configured with output device 59, and can be electronically coupled with embedded computer 16A. Communications among the components could be conducted wirelessly. The use-specific entity could be tailored for such applications as military work, emergency transport, disaster and rescue, expeditions, space explorations, and to aid in medical care in developing countries.

Continuing to refer to FIG. 1, a major aspect of system 100 is its reconfigurability, which is achieved by adhering to the following requirements: (1) embedded computer 16A can be configured with sufficient processing power, for example, multiple processors, in order to execute imaging algorithms required for ultrasound processing; (2) embedded computer 16A can be configured with sufficient memory, for example, >2 gigabytes to manipulate three-dimensional data sets in real-time; (3) system 100 can be configured to operate over a sufficient temperature range, for example, from −10° C. to 45° C., to enable usage in harsh envisioned climatic environments; (4) system 100 can be configured to be weather- and dust-resistant to enable outdoor operation; (5) system 100 can be configured to accommodate ruggedized connectors, such as MIL-SPEC connectors; (6) system 100 can be modular; (7) system 100 can be configured with a hardware co-processor to enable two- and three-dimensional image processing in real-time; (7) system 100 can be configured with a condition-tolerant, relatively low power consumption, relatively fast start storage such as, for example, solid-state disk drives; (8) system 100 can be configured to operate for extended periods of time, for example, >10 hours, on non-grid power; (9) system 100 can be configured to accept data from physiological sensors; (10) system 100 can be configured to support for multiple network interfaces; (11) system 100 can be configured with flexible antenna configurations, for example external antennas, to allow for maximizing antenna geometry for a particular application; (12) system 100 can be configured with an efficient way to manage power consumption, for example a software controlled power supply.

Figure 3:
FIG. 3 is a pictorial diagram of another use-specific entity, a case, and an illustrative component.
Figure 4:
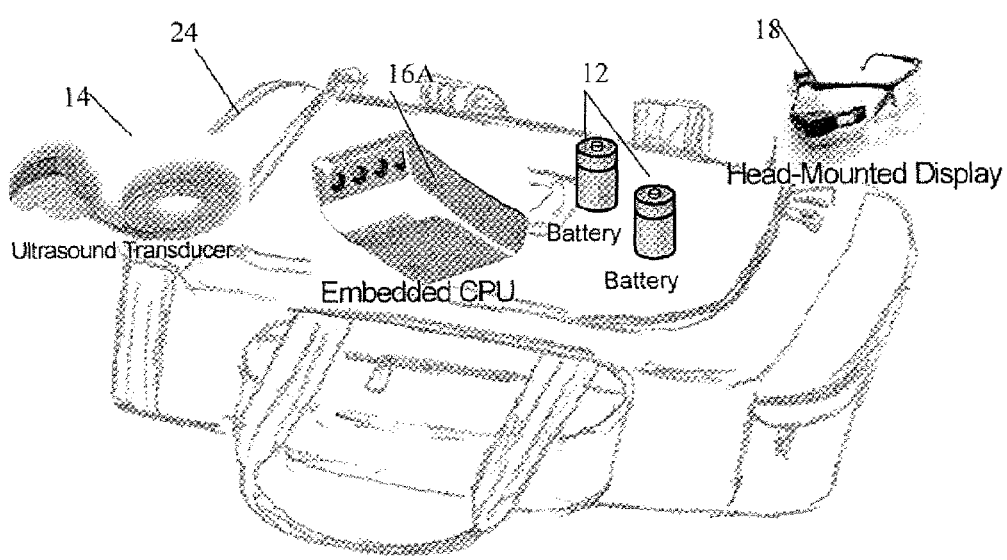
FIG. 4 is a pictorial diagram of illustrative components of the invention in conjunction with a use-specific entity, a case.

Referring now to FIGS. 3 and 4, another use-specific entity, case 24, is shown from the outside and also schematically. The components of system 100, as described with respect to FIGS. 1 and 2, are also shown in FIG. 4. System 100 can be packaged in any of several configurations, whichever is best suited for the given imaging situation. Besides vest 10 and case 24, a belt, for example, containing internally all the necessary cabling, and with the individual components configured in 'fanny bag' type compartments, could be used.

Figure 5A:
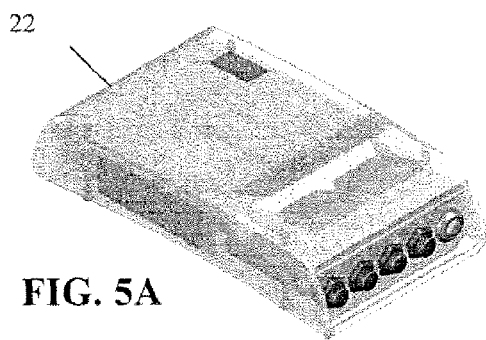
FIG. 5A is a pictorial diagram of an illustrative enclosure of the invention.
Figure 5B:
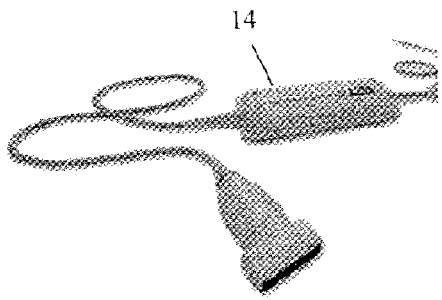
FIG. 5B is a pictorial diagram of an illustrative ultrasound transducer of the invention.
Figure 5C:
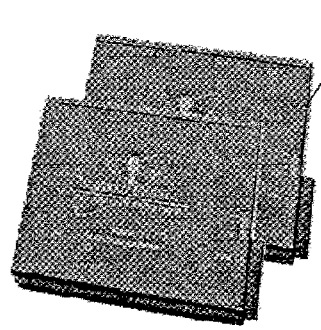
FIG. 5C is a pictorial diagram of illustrative power sources of the invention.
Figure 5D:
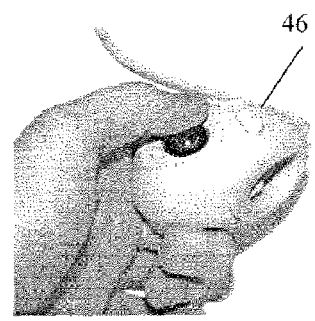
FIG. 5D is a pictorial diagram of an illustrative input device of the invention.
Figure 5E:
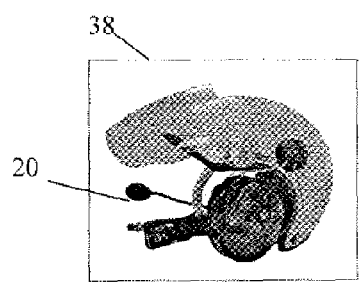
FIG. 5E is a pictorial diagram of an illustrative helmet including illustrative input and output devices.
Figure 5F:
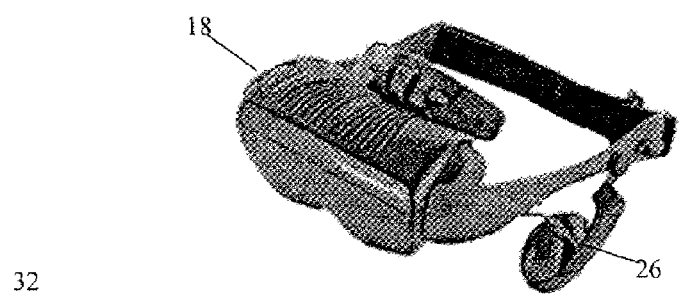
FIG. 5F is a pictorial diagram of an illustrative headset including an illustrative output device.
Figure 5G:
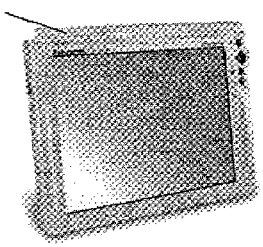
FIG. 5G is a pictorial diagram of an illustrative output device, i.e. a viewing device which is a removable screen.

Referring now to FIGS. 5A-G, possible components of system 100 are pictorially illustrated. FIG. 5A shows illustrative enclosure 22 which can contain embedded computer 16A (FIG. 1). FIG. 5B shows illustrative ultrasound transducer 14, and FIG. 5C shows an illustrative power source, batteries 12. FIG. 5D shows an illustrative input device, computer mouse device 46, and FIG. 5E shows illustrative helmet 38, which can include microphone 20, and FIG. 5F shows illustrative headset 18, which can include earphone 26. FIG. 5G shows an illustrative viewing device 33 (FIG. 8), removable display 32 which can be, for example, a touch screen. Removable display 32 can be configured with a touch keypad. Removable display 32 can be connected in the same manner as the wearable viewer in headset 18. The touch screen, as well as voice data, may be used to annotate image 43, such as, for example, in overlay. Also, the touch screen can be used in the manipulation of on-screen controls. The touch screen data are composited, using alpha blending, onto the images 43 and presented to the user and/or remote viewer as an integrated image. Images 43 can be stored separately from the annotations.

Continuing to refer to FIGS. 5A-G, image and system information viewing can be accomplished through headset 18 or display 32, both of which can be generally referred to as viewing device 33 (FIG. 8) can be used for such purposes as, for example, to view ultrasound images, power source status, patient information, communication equipment status, physiological data 57A, and medical data, among other things. Viewing device 3) (FIG. 8) can be wearable as shown in FIG. 18. The wearable viewer can be equipped with a standard Video Graphics Array (VGA) connection. System 100 can provide a connector that contains a VGA interface. The wearable viewer can be directly connected to the system by a short adapter cable. Power for the wearable viewer can be supplied by a small battery. The VGA connector can be hermetically sealed and can meet MIL-SPEC requirements to ensure that the electronics in sealed section 42A (FIGS. 7A and 7B) are properly sealed and ruggedized. System 100 can accommodate several types of input devices 45 including, but not limited to, a touch screen, microphone 20, a joystick, and a computer mouse device 46.

Figure 6:
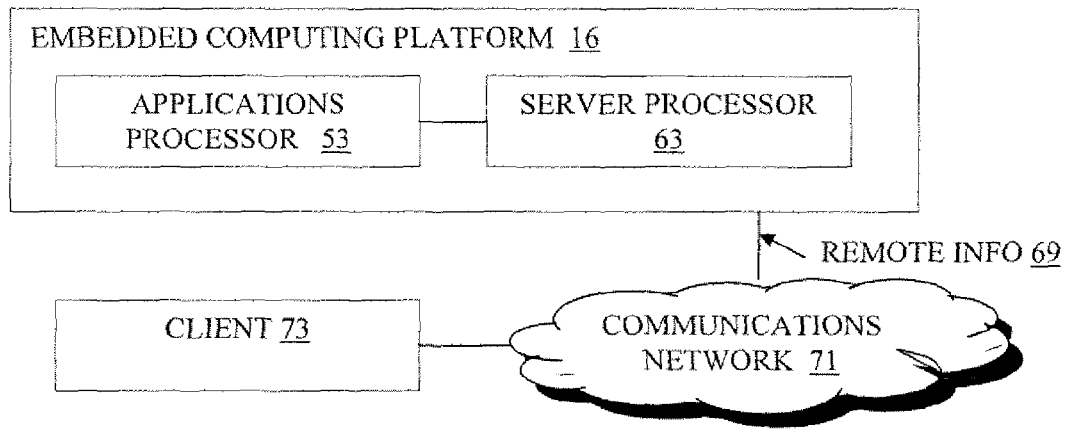
FIG. 6 is a schematic block diagram of an illustrative high-level architecture of the invention.

Referring now to FIG. 6, the environment in which system 100 can execute can include, but is not limited to including, embedded computing platform 16, which can include applications processor 53 and server processor 63. Embedded computing platform 16 can be electronically coupled with communications network 71 to accommodate, for example, receiving remote information 69 from client 73 and sending ultrasound and other data to client 73, among other uses for such a connection, which can be wireless, and can be facilitated by, for example, a standard 802.11 interface, a cellular telephone, or satellite communications such as Globalstar and Inmarsat. System 100 can be controlled by voice commands, and audio can be used for wireless internet connection or two way radio communication, for Doppler sound or for voice annotation of ultrasound images.

Figure 7A:
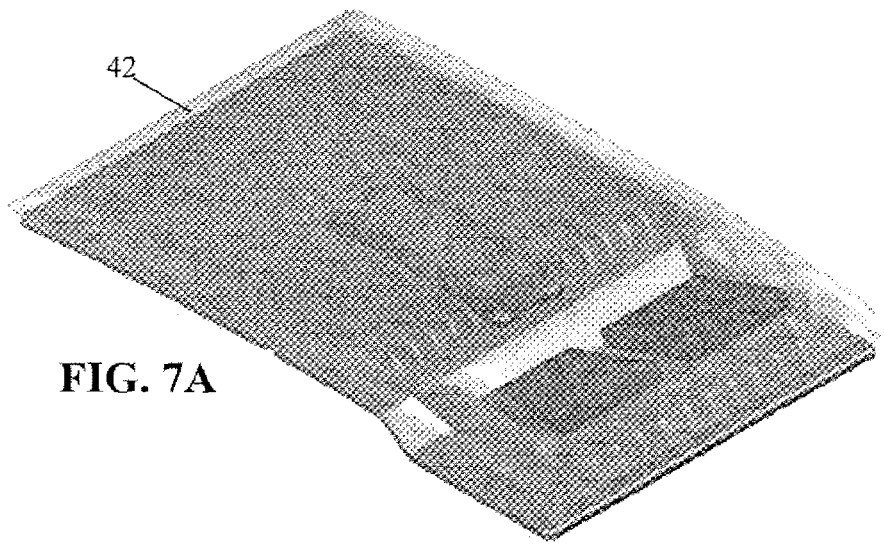
FIG. 7A is a pictorial diagram of an illustrative enclosure of the invention.
Figure 7B:
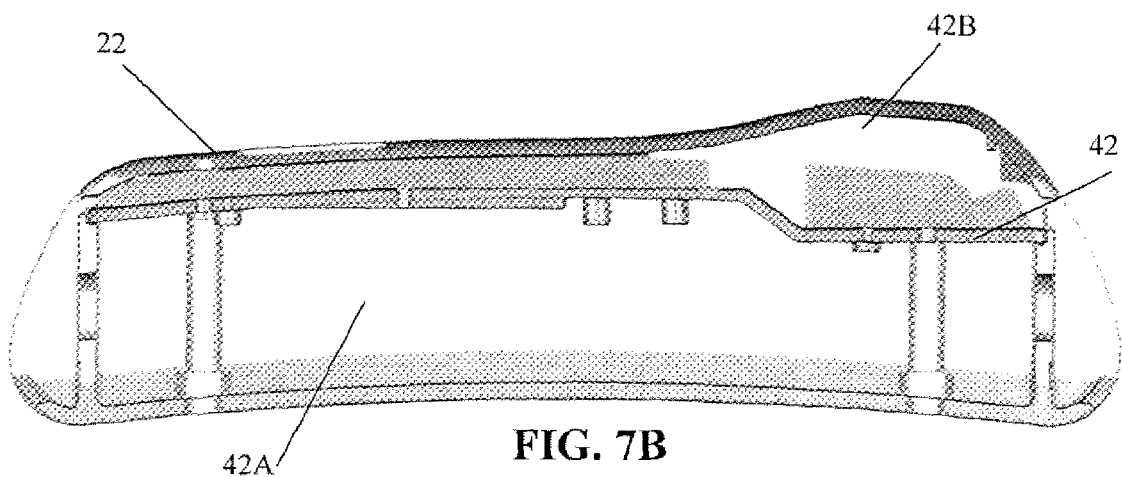
FIG. 7B is a schematic diagram of the inner chambers of an illustrative enclosure of the invention.
Figure 8:
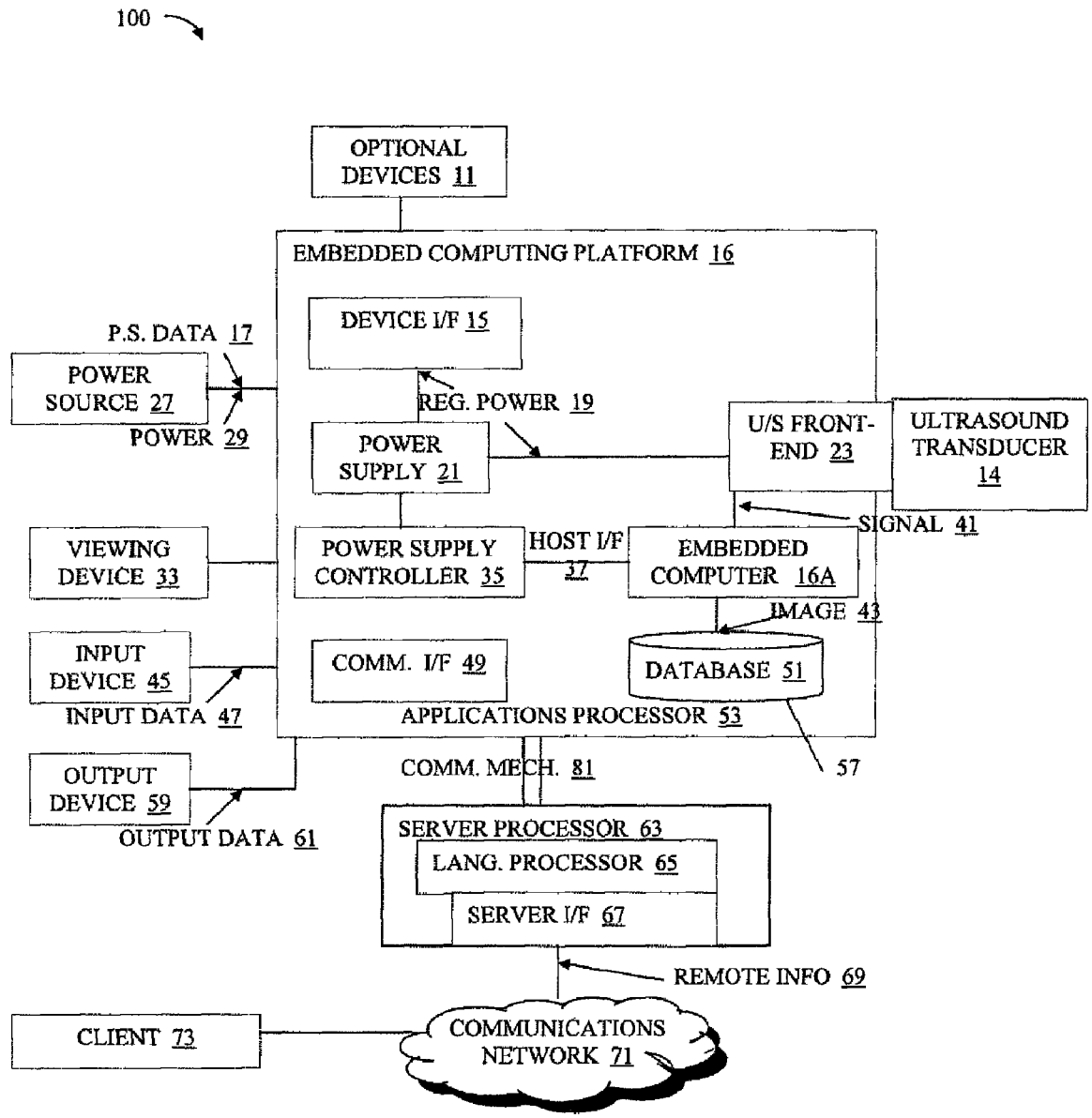
FIG. 8 is a schematic block diagram of an illustrative detailed architecture of the system of the invention.

Referring now to FIGS. 7A and 7B, embedded computing platform 16 can be encapsulated in enclosure 22 to accommodate ruggedization of the device. Enclosure 22 can be separated into multiple, for example two, internal compartments, sealed section 42A and ventilation section 42B. Sealed section 42A can be hermetically sealed and protects all of the sensitive electronics. Ventilation section 42B can contain one or more cooling devices 123 (FIG. 13), for example, two fans, that can be controlled by power supply controller 35 (FIG. 8). Sealed section 42A can be thermally coupled to ventilation section 42B, which can remove excess heat using, for example, passive or forced convection. The forced convection is run at the minimum level required to keep the electronics operating in a safe temperature range to minimize power consumption. Sealed section 42A can be configured to enclose embedded computer 16A, computer-readable medium 57, power supply 21, and power supply controller 35, and ventilation section 42B can be configured with at least one cooling device 123 that can be controlled by cooling device controller 121. System 100 is designed to be used in environments that are normally hostile to medical equipment. FIG. 7B shows the inside of enclosure 22. The electronics of system 100 are located in sealed section 42A, which is separated from ventilation chamber 42B by heat sink 42. Thus, any heat generated by the electronics of system 100 are dissipated by ventilation chamber 42B without exposing the electronics of system 100 to rain, dust and rough handling which could render system 100 useless.

Referring now primarily to FIG. 8, system 100, a ruggedized ultrasound imaging system, can include, but is not limited to including, power supply controller 35 configured to control power supply 21, ultrasound transducer 14 and front end 23 configured to provide signal 41, input device 45 configured to receive input data 47 from a user, and embedded computer 16A electronically coupled with power supply 21, power supply controller 35, ultrasound transducer 14, front end 23, input device 45, output device 59, and computer-readable medium 57. Embedded computer 16A can be configured to receive signal 41 and formulate signal 41 into image 43, receive input data 47 from input device 45, communicate power supply data 17 to power supply 21 and power source 27 through power supply controller 35, and present image 43 on said output device 59, store input data 47 in association with image 43 in database 51 configured to enable retrieval of the associated information. System 100 can also include sealed enclosure 22 (FIGS. 5A and 7B) configured to enclose embedded computer 16A, a computer-readable medium 57, power supply 21, and power supply controller 35. System 100 can still further include a cooling device 123 (FIG. 13) configured to maintain the temperature inside sealed enclosure 22 (FIG. 3). System 100 can further include heat sink 42 (FIGS. 7A and 7B) configured to separate cooling device 123 (FIG. 13) from sealed enclosure 22 (FIGS. 5A and 7B), and a temperature sensor 119A (FIG. 13) configured to control cooling device 123.

Continuing to refer primarily to FIG. 8, system 100 can still further include a use-specific entity, such as vest 10 (FIG. 1) configured to package sealed enclosure 22 (FIG. 2), power source 27, ultrasound transducer 14 (FIG. 1) and front end 23, output device 59, and input device 45. System 100 could also be configured with headset 18 that could be associated with output device 59. System 100 can include wired and wireless communications capabilities, to enable local-type communications such as, for example, among embedded computer 16A, input device 45, and output device 59, and also wide area communications such as, for example, communications between embedded computer 16A and a remote location. System 100 can even still further include a three-dimensional-capable display configured to render three-dimensional images. With respect to three-dimensional capability of this system, PCT/US06/12327, filed on Mar. 30, 2006, is incorporated herein in its entirety by reference. Three-dimensional imaging can include a sensor suite and real-time processing performed on a co-processor to provide timely image orientation information to three-dimensional reconstruction algorithms running within the applications processor 53. The three-dimensional volume can be presented to the user as wither a rendered surface, or a true three-dimensional image, if there exist appropriate display devices, such as a stereo optical head-mounted display, using the system's client software.

Figure 9:
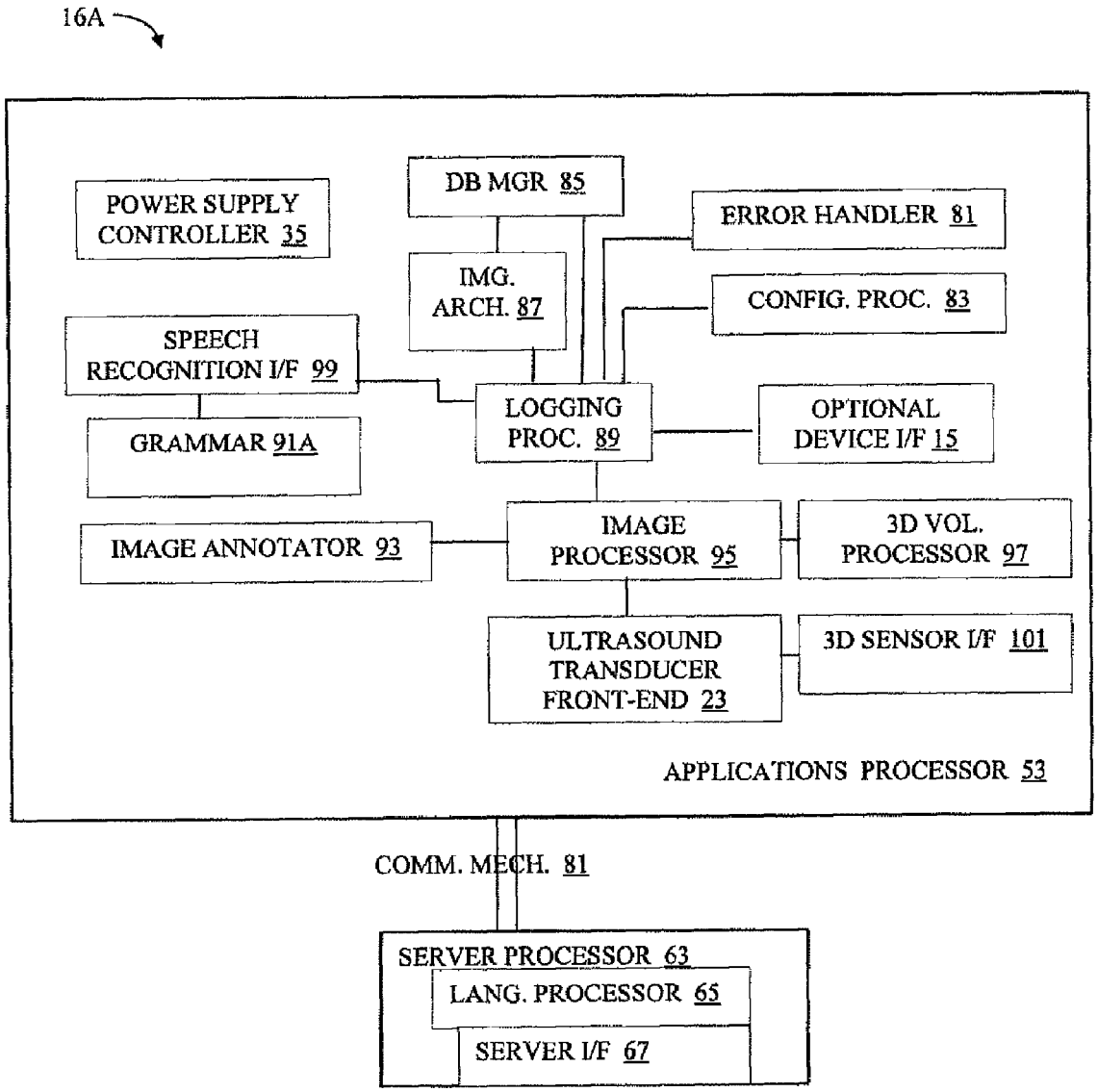
FIG. 9 is a schematic block diagram of an illustrative detailed architecture of an embedded computing platform of the invention.

Referring now to FIG. 9, embedded computer 16A can include, but is not limited to including applications processor 53 and server processor 63. Applications processor 53 can include, but is not limited to including, ultrasound transducer front-end 23 configured to communicate with ultrasound transducer 14, database manager 85 configured to communicate with database 51, image processor 95 configured to receive and transmit image 43, which can include image loops, and other data associated with image 43 such as, for example, audio data, text, and patient information. Applications processor 53 can further include image archiver 87 configured to archive for example, image 43, which can include image loops, physiological data 57A, and medical data, to database 51. Data, such as patient information, metrics and metadata for stored patient images or cine loops, are stored in database 51, for example, a relational database. In one embodiment, images 43, cine loops and voice annotations can be stored on an NTFS partition. In an embodiment, an Applications Programming Interface (API), rather than a query language, can be used to directly access and update database information. Data can be stored and transmitted in compressed form, which may or may not involve data loss. Stored images 43, for example, could be stored in compressed form without any loss of the original data by used of lossless compression such as Portable Network Graphic (PNG). Stored voice annotations, on the other hand, can be stored in compressed form with possible data loss, for example, using a lossy compression format such as GSM 6.10.

Applications processor 53 can also include image annotator 93 configured to associate image 43 with input data 45, logging processor 89 configured to track a plurality of commands 79, configuration processor 83 configured to couple embedded computer 16A with power supply 21, computer-readable medium 57, speech recognition device 98 (FIG. 14), ultrasound transducer 14 (FIG. 1) and front end 23, output device 59 (FIG. 8), and input device 45 (FIG. 8). Applications processor 53 can also include error handler 82 configured to manage failures in embedded computer 16A, three-dimensional volumetric processor 97 configured to present three-dimensional images on output device 59, and three-dimensional sensor interface 101 configured to process three-dimensional data from ultrasound transducer 14 and front end 23, and provide the three-dimensional data to three-dimensional volumetric processor 97. Embedded computer 16A can also include server processor 63 that can include, but is not limited to including, language processor 65 configured to process a language, such as a markup language such as XML, used to enable communications between embedded computer 16A and a remote location, and server interface process 67 configured to transmit messages between embedded computer 16A and a remote location, either through a wired or wireless connection, and communications mechanism 81 configured to provide interprocess communications between said applications processor 53 and server processor 63 by means of, for example, a pipe.

Figure 10A:
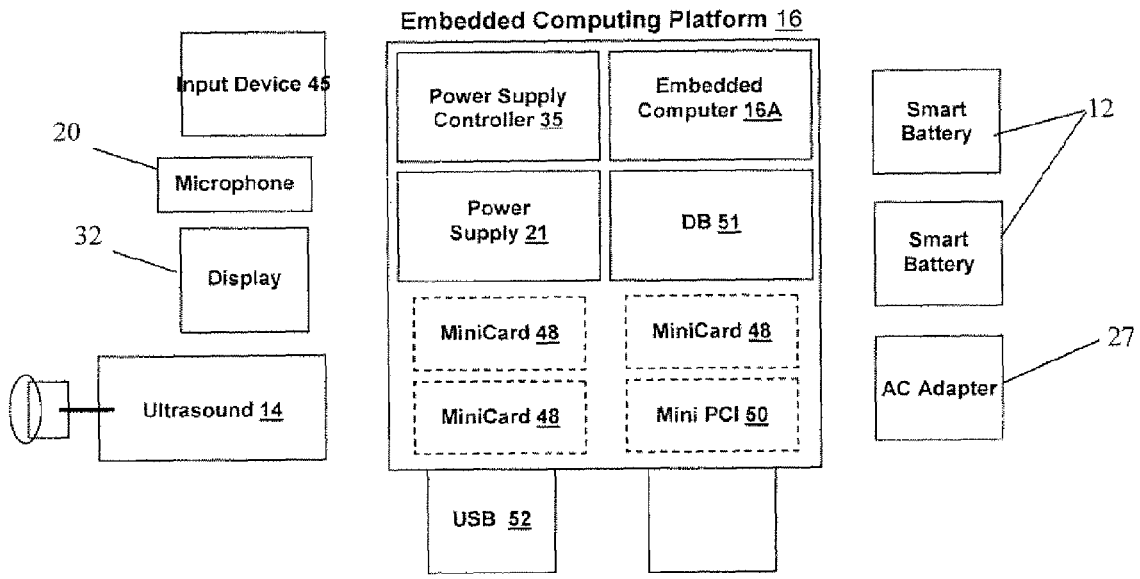
FIG. 10A is a schematic block diagram of an illustrative architecture of an embedded computing platform along with exemplary interface devices.
Figure 10B:
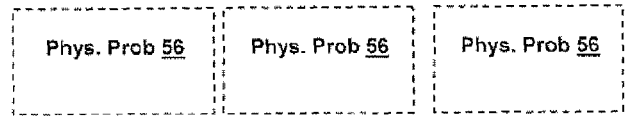
FIG. 10B is a schematic block diagram of an illustrative architecture of an embedded computing platform having physiological sensor interfaces.
Figure 10B:
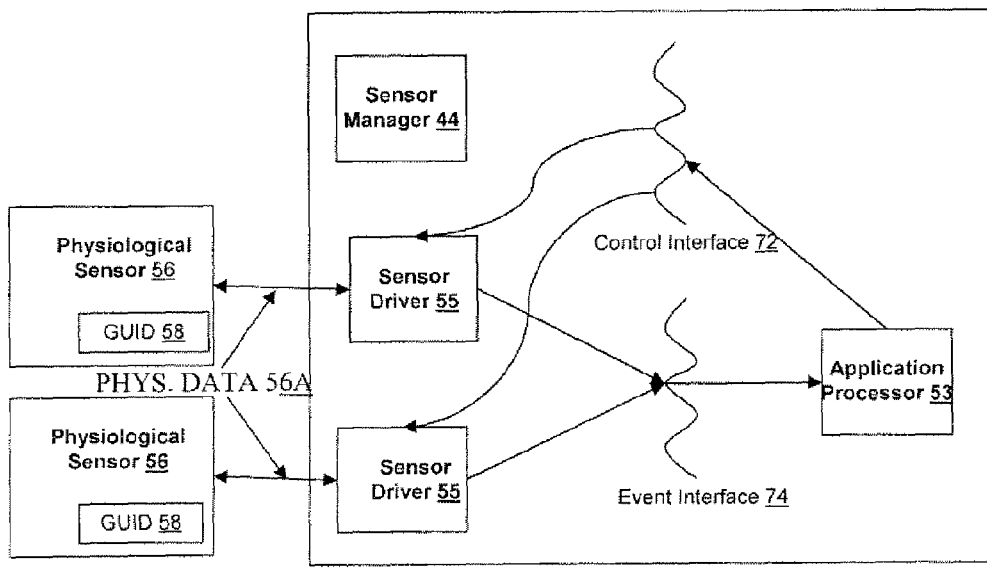
Figure 11:
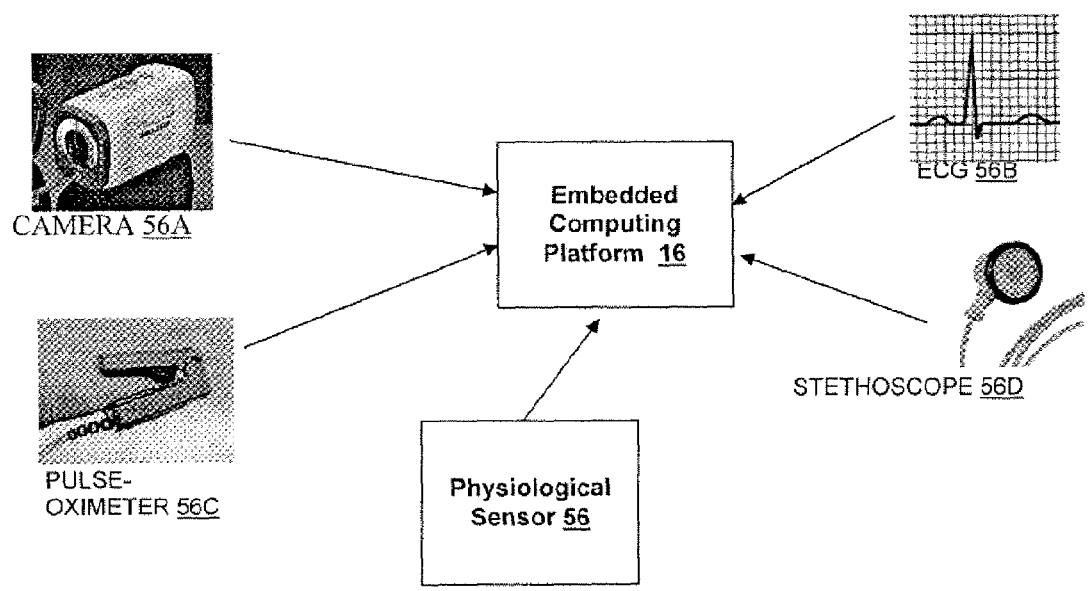
FIG. 11 is a pictorial diagram of an illustrative set of physiological sensors coupled with the embedded computing platform.

Referring now to FIGS. 10A, 10B, and 11, system 100 can further include at least one physiological sensor probe 56 configured to measure physiological data 57A (FIG. 11), and at least one medical device configured to measure medical conditions. Embedded computer 16A can be dynamically reconfigured with other physiological sensor probes, other medical devices, other input devices, and other output devices. Power sources such as batteries 12 can be hot swappable. System 100 can be augmented with additional physiological sensors 56 such as, for example, pulse-oximeter probe 56C (FIG. 11), ECG device 56B (FIG. 11), a spirometer, camera 56A (FIG. 11), a wireless camera, a blood gas analyzer, and stethoscope 56D (FIG. 11). With respect to examination camera 56A (FIG. 11), video data from camera 56A (FIG. 11) can be integrated into the ultrasound display to show the user what camera 56A is seeing. In one embodiment, video from camera 56A (FIG. 11) can be provided by the DirectX API in WINDOWS® and integrated into the display. A remote user, using the client software, can also view this video as an additional video stream. Examination camera 56A (FIG. 11) can be connected to the system by an adapter cable that can convert the composite video provided by camera 56A (FIG. 11) into a USB video device. Camera 56A (FIG. 11) can be powered by a battery.

Referring now to FIG. 10A, power source 27, for example, AC adapter, can convert 120/240 VAC power into 24 VDC power to simultaneously power system 100 and recharge power source 27. Alternatively, the power source can be recharged from solar panels or any other kind of energy source. Smart batteries 12 are batteries with integrated electronics to provide data such as, for example, current voltage and remaining capacity. When input device 45 is configured as microphone 20, system 100 can be augmented by, for example, a conventional microphone, an array microphone, a wireless microphone (Bluetooth or proprietary RF, for example), or a network microphone. Input device 45 can be configured as, for example, a computer mouse, for example, a handheld, optical, mechanical, wireless, or three-dimensional mouse, a touch screen, or a joystick. When output device 59 is configured as viewing device 33 such as a display, system 100 can be augmented by, for example, a conventional video monitor, a television, a head-mounted display, a three-dimensional monitor, a three-dimensional head-mounted display, for example stereo-optical, a network display, a handheld monitor, or a wireless display. MiniCard 48 (a small form factor board used to implement the PCI Express interface on small computers) and Mini PCI 50 (a standard for a computer bus for attaching peripheral devices to a computer motherboard in a small computer) can provide interface functionality for various devices that could be configured with system 100. USB 52 can provide an interface connection for these devices. System 100 can be configured or reconfigured by creating a core platform that can include required and optional devices 11. One embodiment could include a 120 VAC adapter, two smart batteries 12, ultrasound transducer 14 and front end 23, array microphone 20, stereo headphones, a stereo-optical head-mounted display, a handheld computer mouse, all enclosed in case or bag 24. Another embodiment could include a 120 VAC adapter, two smart batteries 12, ultrasound transducer 14 and front end 23, a Bluetooth microphone and speaker, a handheld monitor, a touch screen, all enclosed in a backpack. Thus, the core platform can include one item from, for example, an ultrasound, a front end, a microphone, a speaker, a display, an input device, and a form factor such as, for example a bag or a vest, in addition to an AC adapter, smart batteries, and an embedded computing platform. In addition to the core platform, optional interfaces such as, for example, for ECG, pulse-oximeter, spirometer, and smart stethoscope, and antennas, GPS devices, still cameras, and video cameras can be configured. Additional optional interfaces may require the addition of hardware within the embedded computing platform, including a ruggedized enclosure, such as, for example, a co-processor and wireless processing devices. System 100 can reconfigure itself to accommodate the addition of hardware and other options.

Referring now to FIG. 10B, the reconfigurable nature of physiological sensors 56 can be accomplished using sensor manager 44, and sensor drivers 55 that are specific to each supported physiological sensor 56. Sensor manager 44 can be responsible for selecting the appropriate sensor driver 55 by means of a globally unique identifier (GUID) 58 that is unique for each supported physiological sensor 56. Upon system initialization, for non-hot swappable physiological sensors 56, or upon insertion or removal of a physiological sensor 56, for hot swappable physiological sensors 56, sensor manager 44 can instantiate and configure the appropriate sensor driver 55 for each supported physiological sensor 56. Each sensor driver 55, although specific to a particular physiological sensor 56, can belong to a class of physiological sensors 56. These classes can include pulse-oximeter, ECG, stethoscope, still camera, video camera, etc. Each sensor driver 55 can have the same control interface 72 and event interface 74 for interaction with applications processor 53. Sensor driver 55 can be responsible for translating control and data between the interface for physiological sensor 56 (such as USB, Bluetooth, Wireless-USB, proprietary RF, infrared, FireWire, Mini PCI, etc. . . . ) and control interface 72 and event interface 74 to the applications processor 53. This translation may include data mapping, data translation, and emulation.

Continuing to refer to FIG. 11B, event interface 74 can carry the data from different physiological sensors 56, via sensor driver 55, in events 77 (FIG. 12) that are specific to each class of supported physiological sensors 56. Sensor driver 55 can be responsible for translating the data emanating from physiological sensor 56 into event interface events 77 specific to a particular class of physiological sensors 56. Each event interface data event 77 can carry the GUID 58 of the particular physiological sensor 56, along with a payload that is defined by the class to which the physiological sensor 56 belongs. Other events 77, carried over event interface 74, can contain contextual information about physiological sensor 56, such as, for example, capabilities, vendor information, date of manufacture, etc. . . . , and can state specific information, such as, for example, running, stopped, acquiring, and low battery.

Continuing to still further refer to FIG. 10B, control interface 72 can carry commands 79 and control information from applications processor 53, through sensor driver 55, to physiological sensor 56. Control interface 72 can be specific to each class of physiological sensors 56. Sensor driver 55 can be responsible for translating the command 79 emanating from applications processor 53, through control interface 72, into commands 79 and control information specific to a particular physiological sensor 56. These commands 79 can include, but are not limited to including, start, stop, reset, and increase gain.

Continuing to even still further refer to FIG. 10B, the reconfigurable nature of physiological sensors 56 can be accomplished using a sensor manager 44, and a series of sensor drivers 55 that are specific to each supported physiological sensor 56. A dynamic Graphical User Interface (GUI) can be used to present information on the attached sensors. Data from each sensor can be logged into database 51 for off-line or remote viewing as well as for trend analysis. Physiological sensors 56 can be connected to system 100 by means of a conventional USB port which is also used to power physiological sensor 56. External hardware can be used to adapt physiological sensors 56 that do not include a USB interface. Each physiological sensor 56 can be individually identifiable via an identifier that is unique to every USB peripheral. In one embodiment, applications processor 53 can access the identifier and select an arrangement for displaying the data based on the identifier.

Figure 12:
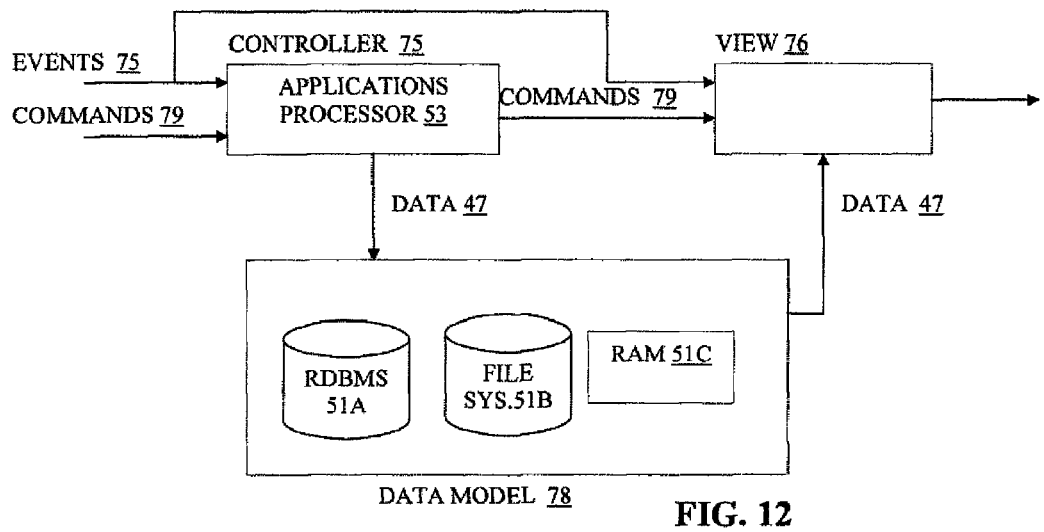
FIG. 12 is a schematic block diagram of an illustrative command and event flow
Figure 14:
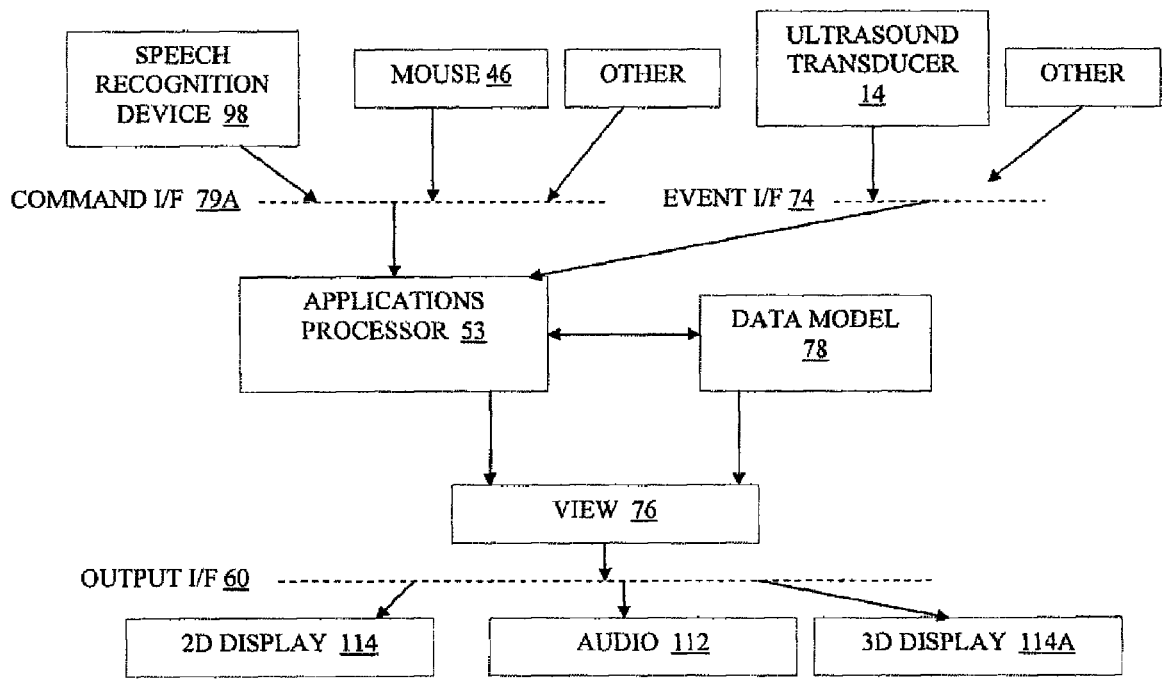
FIG. 14 is a schematic block diagram of an illustrative command and event flow among components of the invention.

Referring now to FIGS. 12 and 14, command 79 can include, but is not limited to including, changing an imaging modality for image 43, changing a focal depth of ultrasound transducer 14, changing a gain of ultrasound transducer 14, changing a color palette of ultrasound transducer 14, entering patient information into database 51, sequencing power source 27 based on power supply data 17, detecting abnormal power conditions based on power supply data 17, correcting abnormal power conditions based on power supply data 17, maintaining power source 27 based on power supply data 17, activating and deactivating cooling device 123 based on the temperature of heat sink 42 and a pre-selected temperature of enclosure 22, and storing images 43 created from signals 41 from ultrasound transducer 14 and front end 23. Controller 75 can control event 77 and command 79 traffic. Speech recognition device 98 and computer mouse 46, for example, can provide commands 79 to applications processor 53 through command interface 79A, while transducer 14, for example, can respond to events 77 generated by applications processor 53 and passing through event interface 74. View 76 can provide data to, for example, two-dimensional display 114, audio 112, or three-dimensional display 114A through output interface 60.

Figure 13:
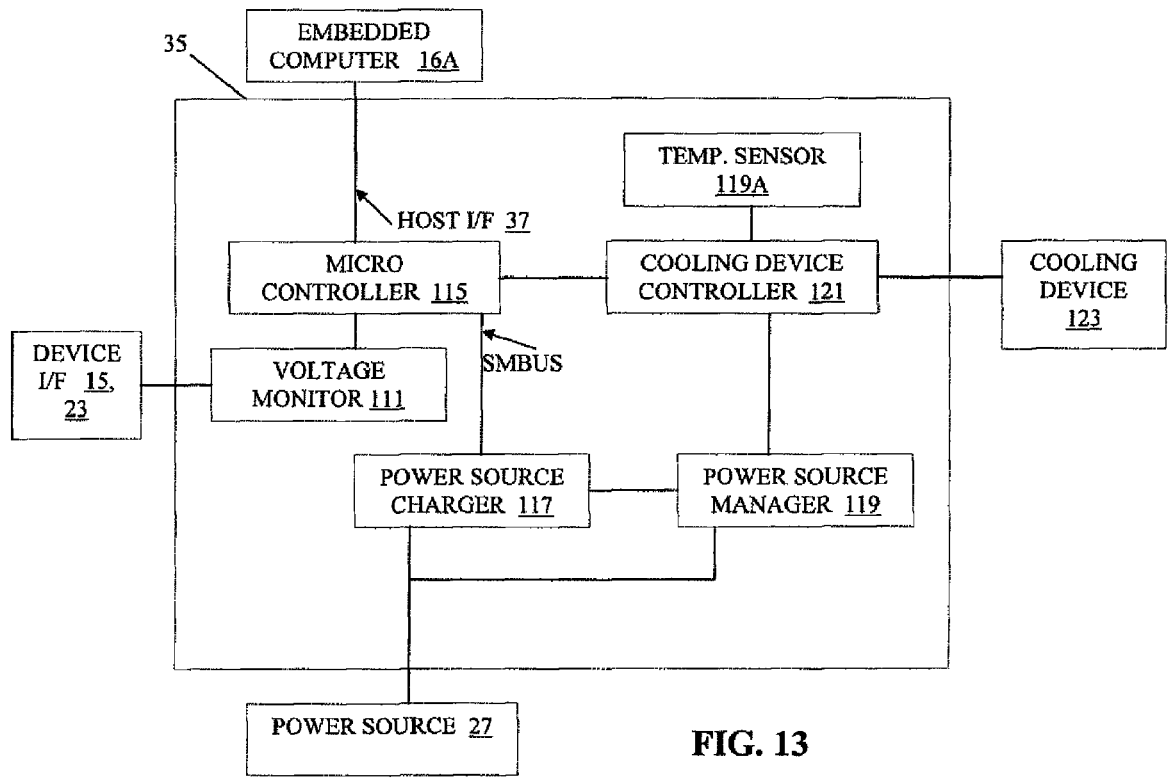
FIG. 13 is a schematic block diagram of an illustrative power supply controller of the invention.

Referring now to FIG. 13, power supply controller 35 can include, but is not limited to including, voltage monitor 111 configured to monitor power supply data 17, host interface 37 configured to receive power supply data 17 from power supply 21 and power source 27, send power supply data 17 to power supply 21 and power source 27, and present power supply data 17 at viewing device 33, microcontroller 115 configured to adjust power supply data 17, power source charger 117 configured to recharge power source 27, temperature sensor 119A configured to measure heat emitted by embedded computer 16A, and cooling device controller 121 configured to control cooling device 123 based on the measured heat and the temperature of heat sink 42.

Continuing to refer to FIG. 13, power supply 21 can include commercial off-the-shelf (COTS) voltage regulators and power supply controller 35 (PSC). PSC 35 can integrate microcontroller 115, voltage monitor 111, host interface 37, cooling device controller 121, temperature sensor 119, and power source charger 117 onto a compact board. Microcontroller 115 can allow software control of voltage regulators to efficiently use the available power 29 (FIG. 8), as well as oversee recharging of power source 27, for example batteries 12 (FIG. 1). Using on-board voltage monitor 111, microcontroller 115 can sequence power sources 27, depending on the operating state of system 100, to achieve the lowest possible power usage. Voltage monitor 111 can serve as a safety device by detecting and correcting abnormal conditions before damaging system 100 or injuring the user. All of the information and events collected by the PSC 35 can be available to embedded computer 16A for monitoring and determining condition-based maintenance scheduling. Condition-based maintenance can determine maintenance intervals based on actual system usage and wear, instead of simply using some measure of operating time.

Continuing to still further refer to FIG. 13, in one embodiment, power can be provided to hardware as needed, depending on operating conditions, and can be managed by power source manager 119. For example, ultrasound transducer 14 can be powered off when not in use. Power can be further reduced by employing a staged power saving approach. System 100 can monitor a user's activity and reduce power consumption accordingly by, for example, hibernating the system. Smart batteries 12 can be used as a portable power source 27. Smart batteries 12 can include a data bus that can be used to set and retrieve the information contained within batteries 12. This information can include, for example, the remaining capacity, current voltage, current draw, and serial number. PSC 35 can include an interface to the data bus, and via host interface 37, applications processor 53 can access power source data 17 (FIG. 8), for example, smart battery information, and provide a graphical display to the user. Power source data 17 can also be used to detect low power conditions and take appropriate action to prevent loss of information and inform the user to swap power source 27 or connect system 100 to an AC adapter. Power source 27 can include a plurality of batteries 12 that are hot swappable.

Figure 15:
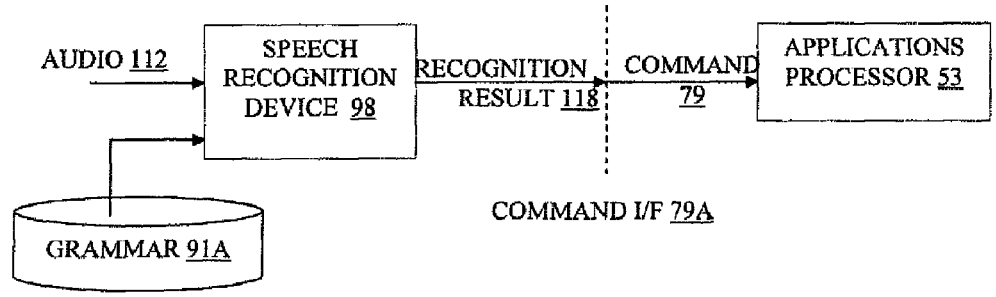
FIG. 15 is a schematic block diagram of an illustrative speech recognition capability of the invention.

Referring now to FIGS. 14 and 15, system 100 can further include speech recognition device 98 configured to receive audio data 112, receive grammar 91A, and provide recognition result 118 and command 79 to embedded computer 16A based on audio data 112 and grammar 91A. Speech recognition device 98 can consume audio samples and can return recognition result 118. Recognition result 118 can be a data structure that can contain, among other things, an assigned number and a string representing what was recognized.

Figure 16:
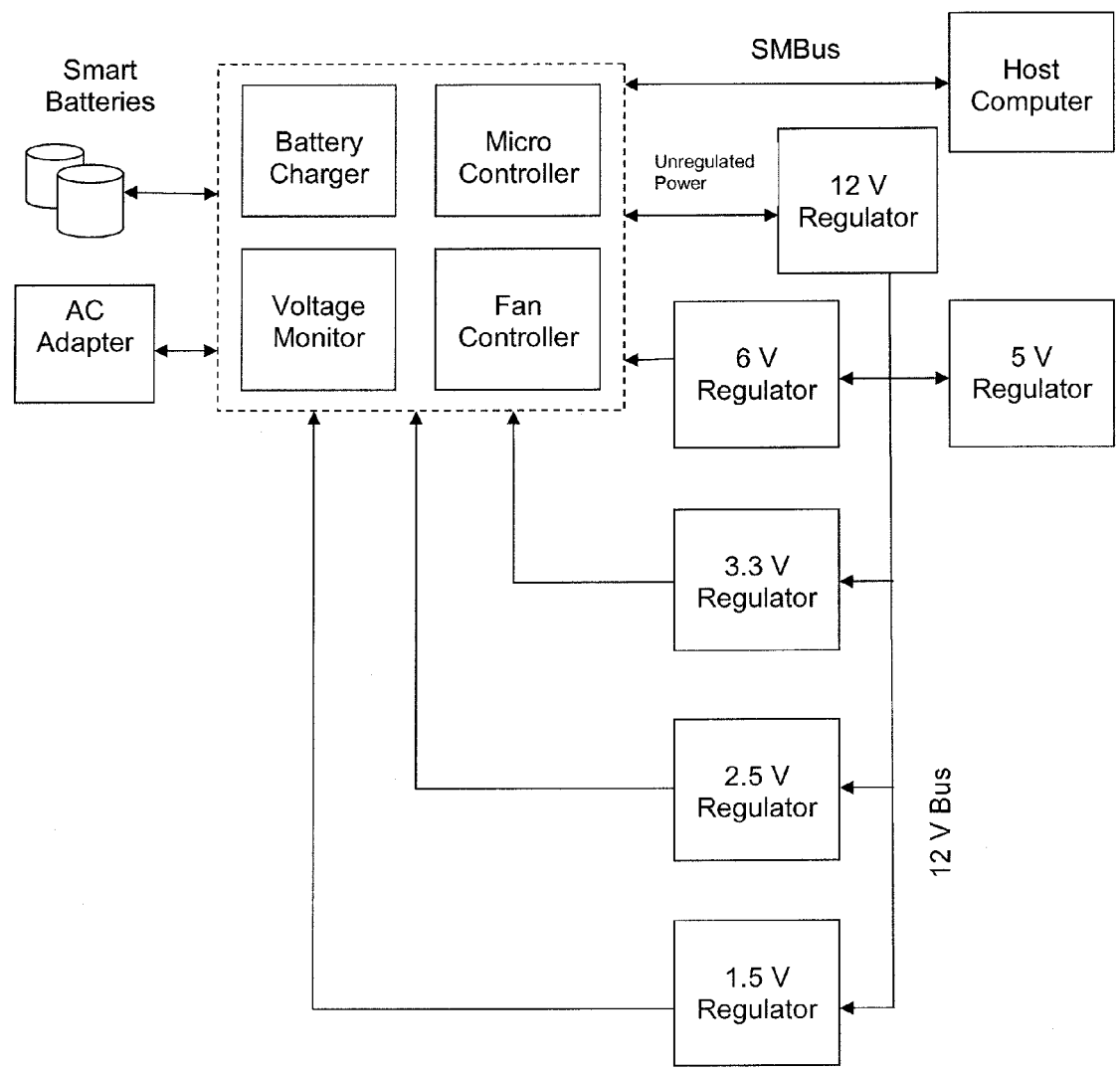
FIG. 16 is a schematic block diagram of an illustrative implementation of the ultrasound system of the invention.

Referring now to FIG. 16, the architecture of an embodiment can include two processes: (1) ISUltrasound which integrates all of the system's software components including speech recognition, power supply monitoring/control, ultrasound interface, physiological sensor interfaces, data management, image processing, remote transmission, archival, annotation, logging, configuration, error handling, server interface to server process, metrics, three-dimensional volumetric imaging/generation/compression/transmission, and three-dimensional sensor interface; and (2) a server process executing in the Sun Java Virtual Machine (JVM), to provide server functionality for telemedicine applications including XML processing, and client interface via Java RMI using TLS security. The server process is connected to the ISUltrasound process via a Windows named pipe for inter-process communication. The ISUltrasound process enables remote clients to connect to the server upon which the process executes. Remote clients can discover the server's location (on a properly configured network). The ISUltrasound process follows a model-view-controller design paradigm. Data model 78 (FIG. 12) is implemented as a combination of a relational database 51A (FIG. 12), a file system 51B (FIG. 12), and in-memory storage RAM 51C (FIG. 12). View 76 (FIG. 12) can include graphical and audio formats locally and remotely. Data such as, for example, ultrasound images 43 (FIG. 8), speech samples, pulse-oximeter data, and ECG data, consumed by applications processor 53 can be carried in the form of events 77 (FIG. 12). Commands 79 (FIG. 12) can originate from sources such as, for example, speech recognition, computer mouse, touch screen, or remotely. The system's client software is accessed using a Java Web Start deployment method, includes functionality to remotely view live ultrasound images and telemetry from physiological sensors, as well as three-dimensional volumes, and provides services for discovering a deployed system on the network. The system itself functions as a server for the client software. The ISUltrasound and Java server processors both perform some actions to reconfigure the system based on network conditions.

Continuing to refer to FIG. 16, the ISUltrasound process uses the commercially-available speech recognition software to implement a speech recognition system. The ISUltrasound process implements software to acquire speech data from a microphone (either hardwired or Bluetooth), pass the data to the commercially-available speech recognition engine, and then perform some action based on the recognition result. Some of the specific actions that can be performed by the speech recognition interface 99 include changing the current imaging modality (B-Mode, M-Mode, Color Doppler, etc.), changing the current focal depth, changing the gain, changing the color palette, and entering patient information. Voice commands can be used to control any aspects of the system where voice command may be appropriate. In one embodiment, the commercially-available speech recognition engine 98 relies on a grammar file, written in augmented Backus-Naur format (BNF+), a format that specifies a context-free language, to generate the language that can be recognized by the speech recognition engine 98. In this embodiment, the speech recognition engine 98 requires no training to use, it is speaker independent, but is limited to understanding a language defined by the grammar. By confining the language to only those particular sentences that are relevant for a given situation, the accuracy of the speech recognition engine 98 is increased. In this embodiment, a dynamic grammar is use so that, for example, when using a command that requires a "yes" or "no" response to confirm an action, a grammar containing only the sentences "yes" or "no" is activated. In this embodiment, an integer is assigned to any particular sentence in the grammar. Upon obtaining a successful recognition result, the integer is used to dispatch a command. This allows for multiple sentences to result in the same command.

Figure 17A:
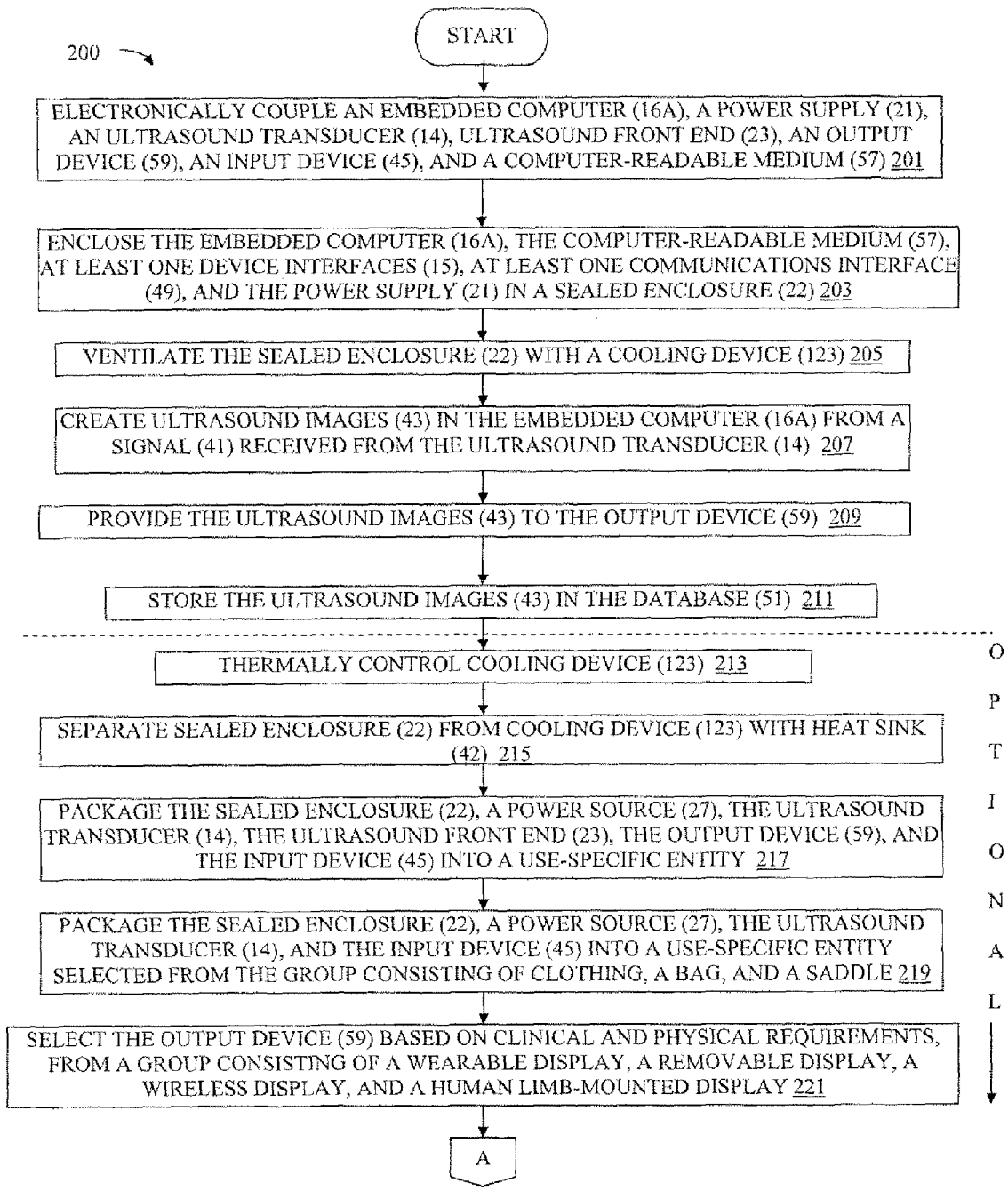
FIGS. 17A and 17B are flowcharts of an illustrative method of the invention.

Referring now primarily to FIG. 17A, method 200 (FIG. 17A) for ruggedized ultrasound imaging can include, but is not limited to, the steps of electronically coupling 201 (FIG. 17A) embedded computer 16A (FIG. 8), power supply 21 (FIG. 8), ultrasound transducer 14 (FIG. 8), ultrasound front end 23 (FIG. 8), output device 59 (FIG. 8), input device 45 (FIG. 8), and computer-readable medium 57 (FIG. 8); enclosing 203 (FIG. 17A) embedded computer 16A (FIG. 8), computer-readable medium 57 (FIG. 8), at least one device interface 15 (FIG. 8), at least one communications interface 49 (FIG. 8), and power supply 21 (FIG. 8) in a sealed enclosure 22 (FIG. 8); maintaining 205 (FIG. 17A) the temperature inside sealed enclosure 22 (FIG. 8) with an external cooling device 123 (FIG. 8); creating 207 (FIG. 17A) ultrasound images 43 (FIG. 8) in embedded computer 16A (FIG. 8) from signal 41 (FIG. 8) received from front end 23 (FIG. 8) and ultrasound transducer 14 (FIG. 8); providing 209 (FIG. 17A) ultrasound images 43 (FIG. 8) to output device 59 (FIG. 8); and storing 211 (FIG. 17A) ultrasound images 43 (FIG. 8) in database 51 (FIG. 8). Method 200 (FIG. 17A) can further include the steps of thermally controlling 213 (FIG. 17A) the temperature of enclosure 22 (FIG. 8) by cooling device 123 (FIG. 8), and separating 215 (FIG. 17A) sealed enclosure 22 (FIG. 8) from cooling device 123 (FIG. 8) with heat sink 42 (FIG. 8). Method 200 (FIG. 17A) can further include the step of configuring 217 (FIG. 17A) sealed enclosure 22 (FIG. 8), power source 27 (FIG. 8), ultrasound transducer 14 (FIG. 8), ultrasound front end 23 (FIG. 8), output device 59 (FIG. 8), and input device 45 (FIG. 8) into a use-specific entity. Method 200 (FIG. 17A) can still further include the steps of configuring 219 (FIG. 17A) sealed enclosure 22 (FIG. 8), power source 27 (FIG. 8), ultrasound transducer 14 (FIG. 8), front end 23 (FIG. 8), and input device 45 (FIG. 8) into a use-specific entity selected from the group consisting of clothing, a bag, and a saddle; and selecting 221 (FIG. 17A) output device 59 (FIG. 8), based on clinical and physical requirements, from a group consisting of a wearable display, a removable display, a wireless display and a human limb-mounted display.

Figure 17B:
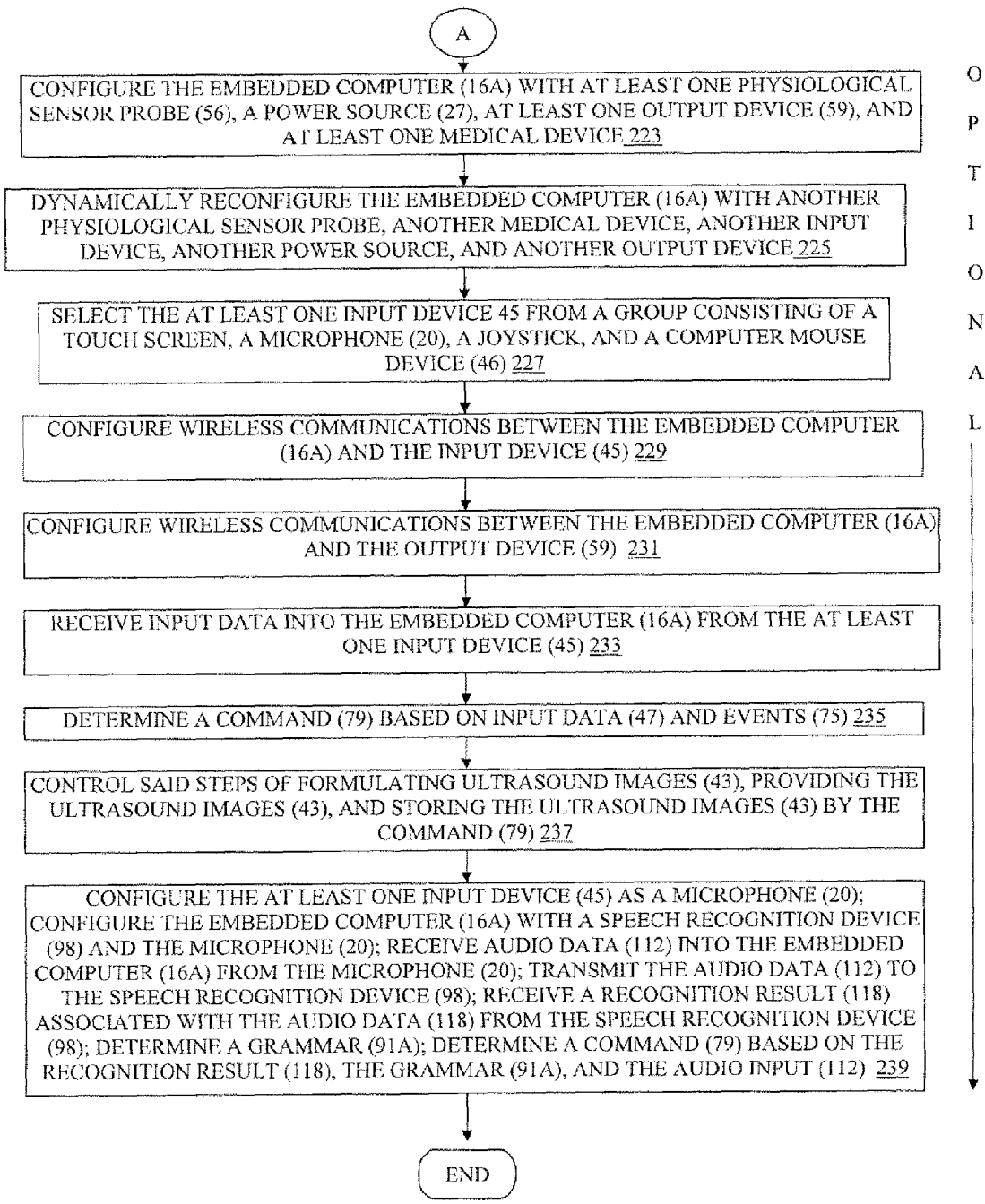

Referring now primarily to FIG. 17B, method 200 can further include the steps of configuring 223 (FIG. 17B) embedded computer 16A (FIG. 8) with at least one physiological sensor 56 (FIG. 8), power source 27 (FIG. 8), at least one output device 59 (FIG. 8), and at least one medical device; and dynamically reconfiguring 225 (FIG. 17B) embedded computer 16A (FIG. 8) with another physiological sensor, another medical device, another input device, and another output device. Dynamically reconfiguring is herein defined to mean that one device, for example physiological sensor 56 (FIG. 8), can be exchanged for another physiological sensor without restarting system 100 (FIG. 8). Method 200 (FIG. 17) can further include the steps of selecting 227 (FIG. 17B) the at least one input device 45 (FIG. 8) from a group consisting of a touch screen, microphone 20 (FIG. 8), a joystick, and computer mouse device 46 (FIG. 8), configuring 229 (FIG. 17B) wireless communications between embedded computer 16A (FIG. 8) and input device 45 (FIG. 8), and configuring 231 (FIG. 17B) wireless communications between embedded computer 16A (FIG. 8) and output device 59 (FIG. 8). Method 200 (FIG. 17) can further include the steps of receiving 233 (FIG. 17B) input data into the embedded computer 16A (FIG. 8) from at least one input device 45 (FIG. 8), determining 335 (FIG. 17B) command 79 (FIG. 8) based on input data 47 (FIG. 8) and events 77 (FIG. 8), and controlling 237 (FIG. 17B) the steps of formulating ultrasound images 43 (FIG. 8), providing ultrasound images 43 (FIG. 8), and storing ultrasound images 43 (FIG. 8) by command 79 (FIG. 8). Method 200 (FIG. 17B) can further include the steps of configuring 239 (FIG. 17B) at least one input device 45 (FIG. 8) as microphone 20 (FIG. 8), configuring embedded computer 16A (FIG. 8) with speech recognition device 98 (FIG. 8) and microphone 20 (FIG. 8), receiving audio data 112 (FIG. 8) into embedded computer 16A (FIG. 8) from microphone 20 (FIG. 8), transmitting audio data 112 (FIG. 8) to speech recognition device 98 (FIG. 8), receiving recognition result 118 (FIG. 8) associated with audio data 112 (FIG. 8) from speech recognition device 98 (FIG. 8), determining grammar 91A (FIG. 8), and determining command 79 (FIG. 8) based on recognition result 118 (FIG. 8), grammar 91A (FIG. 8), and audio data 112 (FIG. 8).

Method 200 (FIG. 17A) can also include the optional steps of configuring the embedded computer 16A (FIG. 8) with power supply controller 35 (FIG. 8) for controlling power supply 21 (FIG. 8), receiving power supply data 17 (FIG. 8) from power supply 21 (FIG. 8) and power source 27 (FIG. 8) through power supply controller 35 (FIG. 8), electronically coupling power source 27 (FIG. 8) with power supply 21 (FIG. 8), sequencing the use of power source 27 (FIG. 8) based on power supply data 17 (FIG. 8), detecting abnormal power conditions based on power supply data 17 (FIG. 8), correcting abnormal power conditions based on power supply data 17 (FIG. 8), maintaining power source 27 (FIG. 8) based on power supply data 17 (FIG. 8), and activating and deactivating the cooling device 123 (FIG. 8) based on the temperature of heat sink 42 (FIG. 8) and a pre-selected temperature of enclosure 22 (FIG. 8). Method 200 (FIG. 8) can further include the step of configuring viewing device 33 (FIG. 8) as a three-dimensional display for viewing of surface rendered three-dimensional images.

Referring primarily to FIGS. 17A and 17B method 200 can be, in whole or in part, implemented electronically. Signals representing actions taken by elements of the system can travel over electronic communications. Control and data information can be electronically executed and stored on computer-readable media 57 (FIG. 8). System 100 (FIG. 1) can be implemented to execute on embedded computing platform (node) 16 (FIG. 8) in communications network 71 (FIG. 8). Common forms of computer-readable media 57 (FIG. 8) can include, but are not limited to, for example, a floppy disk, a flexible disk, a hard disk, magnetic tape, or any other magnetic medium, a CDROM or any other optical medium, punched cards, paper tape, or any other physical medium with, for example, patterns of holes, a RAM, a PROM, and EPROM, a FLASH-EPROM, or any other memory chip or cartridge, a carrier wave, or any other medium from which a computer can read.

The integrated data and image management system can be configured so that a central person ('expert') can log on to system 100. The 'expert' can observe what a physician or EMT, doing the scanning, is currently observing, or the 'expert' can view the pre-stored images and/or video clips. Alternatively, the scanning may be guided by a remote 'expert', who can monitor and guide the operator as to which images to capture. In another embodiment, system 100 can be used for teaching, so that the person who is scanning is broadcasting image information to many observers or students.

Auxiliary 'slave' display types can be accommodated, instead of or in addition to the head mounted display. One form of a display might be a PDA type device, which can be attached to the left arm and wirelessly communicate with the ultrasound device. Such a PDA may serve many additional purposes, such as reference material or medical history taking. A larger 'slave' display (such as a laptop) may also be used for training or group discussions. With adequate bandwidth available, real time images from any version of the system 100 can be streamed to a remote expert for interpretation and guidance in scanning. In one embodiment, batteries 12 can have a capacity of 200 watt-hours or higher in order to deliver sufficient power for a full day of operation. In one embodiment, heat sink 42 is a heavy-duty, aluminum plate. Many forms of microphones 20 can be used with system 100 as long as they meet requirements such as, for example, performing under noisy conditions and being unobtrusive. Likewise, many types of displays can be used with system 100 as long as they meet requirements such as, for example, weight restrictions, image quality requirements, resolution requirements, brightness requirements, and headphones requirements. The display can be configured to be moved out of view for an unobstructed view of the physical world. System 100 can be compatible with a Personal Information Carrier (PIC) which is a physical, portable, electronic mechanism designed to store the essential elements of a soldier's personal medical history so they can be readily accessed and updated by first responder medical personnel via laptop or hand-held computers when real-time connectivity to a database is unavailable. System 100 can include three-dimensional viewing on a three-dimensional-capable display such as, for example, a stereo-optical head-mounted display.

Although the invention has been described with respect to various embodiments, it should be realized that this invention is also capable of a wide variety of further and other embodiments.

What is claimed is:

1. A method for ruggedized ultrasound imaging comprising the steps of:
   electronically coupling an embedded computer, a power supply, an ultrasound transducer, ultrasound front end, an output device, an input device, and a computer-readable medium;
   enclosing the embedded computer, the computer-readable medium, at least one device interface, at least one communications interface, and the power supply in a sealed enclosure;
   maintaining the temperature inside the sealed enclosure with a cooling device;
   creating ultrasound images in the embedded computer from a signal received from the front end and the ultrasound transducer;
   providing the ultrasound images to the output device;
   storing the ultrasound images in a database;
   configuring the embedded computer with a power supply controller for controlling the power supply;
   receiving power supply data from the power supply and the power source through the power supply controller;
   electronically coupling a power source with the power supply;
   sequencing the use of the power source based on the power supply data;
   detecting abnormal power conditions based on the power supply data;
   correcting abnormal power conditions based on the power supply data;
   maintaining the power source based on the power supply data; and
   activating and deactivating the cooling device based on the temperature of the heat sink and a pre-selected temperature of the enclosure.

2. The method of claim 1 further comprising the steps of:
   thermally controlling the temperature of the enclosure by the cooling device; and
   separating the sealed enclosure from the cooling device with a heat sink.

3. The method of claim 1 further comprising the step of:
   configuring the sealed enclosure, a power source, the ultrasound transducer, the ultrasound front end, the output device, and the input device into a use-specific entity.

4. The method of claim 1 further comprising the steps of:
   configuring the sealed enclosure, a power source, the front end, the ultrasound transducer, and the input device into a use-specific entity selected from the group consisting of clothing, a bag, and a saddle; and
   selecting the viewing device, based on clinical and physical requirements, from a group consisting of a wearable display, a removable display, a wireless display and a human limb-mounted display.

5. The method of claim 1 further comprising the steps of:
   configuring the embedded computer to operate with at least one physiological sensor probe, a power source, at least one output device, and at least one medical device; and
   dynamically reconfiguring the embedded computer to operate with another physiological sensor probe, another medical device, another input device, and another output device.

6. The method of claim 1 further comprising the steps of:
   selecting the at least one input device from a group consisting of a touch screen, a microphone, a joystick, and a computer mouse device.

7. The method of claim 1 further comprising the steps of:
   configuring wireless communications between the embedded computer and the input device;
   configuring wireless communications between the embedded computer and the viewing device.

8. The method of claim 1 further comprising the steps of:
   receiving input data into the embedded computer from the at least one input device;
   determining a command based on input data and events; and
   controlling said steps of formulating ultrasound images, providing the ultrasound images, and storing the ultrasound images by the command.

9. The method of claim 8 further comprising the steps of:
   configuring the at least one input device as a microphone;
   configuring the embedded computer to operate with a speech recognition device and the microphone;
   receiving audio data into the embedded computer from the microphone;
   transmitting the audio data to the speech recognition device;
   receiving a recognition result associated with the audio data from the speech recognition device;
   determining a grammar; and determining a command based on the recognition result, the grammar, and the audio input.

10. The method of claim 1 further comprising the steps of: configuring the viewing device as a 3D display for viewing of surface rendered 3D images.

11. A ruggedized ultrasound imaging system comprising:
a power supply controller configured to control a power supply;
an ultrasound transducer and front end configured to provide a signal;
an input device configured to receive input data from a user;
an embedded computer electronically coupled with said power supply, said power supply controller, said ultrasound transducer, said input device, an output device, and a computer-readable medium, said embedded computer being configured to:
receive said signal and formulate said signal into an image;
receive said input data from said input device;
communicate power supply data to said power supply and a power source through said power supply controller;
present said image on said viewing device; and
store said input data in association with said image in a database configured to enable retrieval of the associated information;
a sealed enclosure configured to enclose said embedded computer, a computer-readable medium, said power supply, and said power supply controller;
a cooling device configured to maintain the temperature inside said sealed enclosure;
a speech recognition device configured to receive audio data, said speech recognition device configured to
receive a grammar; and
provide a recognition result and command to said embedded computer based on said audio data and said grammar; and
wherein said power supply controller comprises
a voltage monitor configured to monitor power supply data;
a host interface configured to
receive said power supply data from said power supply and said power source;
send said power supply data to said power supply and said power source; and
present said power supply data at said viewing device;
a microcontroller configured to adjust said power supply data;
a power source charger configured to recharge said power source;
a temperature sensor configured to measure heat emitted by said embedded computer; and
a cooling device controller configured to control a cooling device based on the measured heat.

12. The system of claim 11 further comprising:
a heat sink configured to separate said cooling device from said sealed enclosure; and
a temperature sensor configured to control cooling activity by said cooling device.

13. The system of claim 11 further comprising:
a use-specific entity configured to package said sealed enclosure, said power source, said ultrasound transducer, said viewing device, and said input device.

14. The system of claim 11 further comprising:
a use-specific entity configured to package said sealed enclosure, said power source, said ultrasound transducer, and said input device; and
an output device selected from a group consisting of a wearable display, a removable display, a wireless display and a human limb-mounted display.

15. The system of claim 11 further comprising:
at least one physiological sensor probe configured to measure physiological data; and
at least one medical device configured to measure medical conditions;
wherein said embedded computer is dynamically reconfigured with another physiological sensor probe, another medical device, another input device, another power source, and another output device.

16. The system of claim 11 further comprising:
a wireless communications interface configured to provide data transmission between said embedded computer and said input device, and between said embedded computer and said output device.

17. The system of claim 11 wherein said input device is selected from a group consisting of a touch screen, a microphone, a joystick, and a computer mouse device.

18. The system of claim 11 wherein said embedded computer is further configured with:
an applications processor including:
an ultrasound transducer front-end configured to communicate with said ultrasound transducer;
a database manager configured to communicate with said database;
an image processor configured to receive and transmit said image;
an image archiver configured to archive said image and physiological data to said database;
an image annotator configured to associate said image with said input data;
a logging processor configured to track a plurality of commands provided by the speech recognition processor;
a configuration processor configured to couple said embedded computer with said power supply, a computer-readable medium, said speech recognition device said ultrasound transducer, said output device, and said input device;
an error handler configured to manage failures in said embedded computer;
a three-dimensional volumetric processor configured to present three-dimensional images on said output device; and
a three-dimensional sensor interface configured to process three-dimensional data from said ultrasound transducer and provide the three-dimensional data to said three-dimensional volumetric processor;
a server processor including:
an language processor configured to process a language used to enable communications between said embedded computer and a remote location; and
a server interface process configured to transmit messages between said embedded computer and said remote location; and
a communications mechanism configured to provide inter-process communications between said applications processor and said server processor.

19. The system of claim 11 further comprising:
an enclosure configured to protect said embedded computer, said enclosure including:
a sealed section configured to enclose said embedded computer, said computer-readable medium, said power supply, and said power supply controller; and
a ventilation section configured with at least one cooling device controlled by said cooling device controller.

20. The system of claim 11 further comprising:
a use-specific entity configured to hold said enclosure, said power supply, said input device, said front end, and said ultrasound transducer; and
a headset configured with said output device, said headset being electronically coupled with said embedded computer.

21. The system of claim 11 wherein said command includes:
changing an imaging modality for said image;
changing a focal depth of said ultrasound transducer;
changing a gain of said ultrasound transducer;
changing a color palette of said ultrasound transducer;
entering said patient information into said database;
sequencing said power source based on said power supply data;
detecting abnormal power conditions based on said power supply data;
correcting said abnormal power conditions based on said power supply data;
maintaining said power source based on said power supply data;
activating and deactivating said cooling device based on said power supply data; and
storing images from said ultrasound transducer.

22. The system of claim 11 further comprising:
a three-dimensional-capable display configured to render three-dimensional images.

23. The system of claim 11 wherein said power source includes a plurality of batteries, said batteries being hot swappable.

24. The system of claim 15 wherein said physiological sensor probe is selected from a group consisting of a pulse-oximeter probe, an ECG device, a spirometer, a camera, a wireless camera, a blood gas analyzer, and a stethoscope.

* * * * *

UNITED STATES PATENT AND TRADEMARK OFFICE
CERTIFICATE OF CORRECTION

PATENT NO. : 8,221,324 B2
APPLICATION NO. : 12/299540
DATED : July 17, 2012
INVENTOR(S) : Peder C. Pedersen et al.

Page 1 of 1

It is certified that error appears in the above-identified patent and that said Letters Patent is hereby corrected as shown below:

In Column 16, line 38 (claim 18), "speech recognition device said" should read -- speech recognition device, said --

Signed and Sealed this
Eleventh Day of September, 2012

David J. Kappos
*Director of the United States Patent and Trademark Office*